(12) United States Patent
Gridelet et al.

(10) Patent No.: US 8,794,054 B2
(45) Date of Patent: Aug. 5, 2014

(54) SENSOR DEVICE AND A METHOD OF MANUFACTURING THE SAME

(75) Inventors: Evelyne Gridelet, Seraing (BE); Pablo Garcia Tello, Leuven (BE); Michiel Jos Van Duuren, Valkenswaard (NL); Nader Akil, Sterrebeek (BE)

(73) Assignee: NXP, B.V., Eindhoven (NL)

( * ) Notice: Subject to any disclaimer, the term of this patent is extended or adjusted under 35 U.S.C. 154(b) by 324 days.

(21) Appl. No.: 13/262,628

(22) PCT Filed: Mar. 25, 2010

(86) PCT No.: PCT/IB2010/051317
§ 371 (c)(1),
(2), (4) Date: Nov. 3, 2011

(87) PCT Pub. No.: WO2010/113090
PCT Pub. Date: Oct. 7, 2010

(65) Prior Publication Data
US 2012/0060589 A1    Mar. 15, 2012

(30) Foreign Application Priority Data
Apr. 3, 2009    (EP) ..................... 09157350

(51) Int. Cl.
*G01N 29/036*    (2006.01)
(52) U.S. Cl.
USPC ......................... 73/61.61; 73/24.06
(58) Field of Classification Search
USPC ............ 73/61.61, 61.75, 74.53, 24.06, 24.01; 310/313 B, 313 D, 313 R
See application file for complete search history.

(56) References Cited

U.S. PATENT DOCUMENTS

| | | | |
|---|---|---|---|
| 5,795,782 A | 8/1998 | Church et al. | |
| 6,627,067 B1 | 9/2003 | Branton et al. | |
| 7,389,673 B2 * | 6/2008 | Kimura et al. | 73/24.06 |
| 7,417,418 B1 * | 8/2008 | Ayliffe | 324/71.1 |
| 7,553,730 B2 * | 6/2009 | Barth et al. | 438/270 |
| 7,867,782 B2 * | 1/2011 | Barth | 436/518 |
| 2005/0019784 A1 * | 1/2005 | Su et al. | 435/6 |

FOREIGN PATENT DOCUMENTS

EP    1 486 775 A1    12/2004
EP    1 788 385 A1    5/2007

OTHER PUBLICATIONS

Rhee, M. et al. "Nanopore Sequencing Technology: Research Trends and Applications", ScienceDirect, Trends in Biotechnology, vol. 24, No. 12, 7 pgs. (Oct. 19, 2006).
Rhee, M. et al. "Nanopore Sequencing Technology: Nanopore Preparation", ScienceDirect, Trends in Biotechnology, vol. 25, No. 4, 8 pgs. (Feb. 22, 2007).
Dekker, C. "Solid-State Nanopore", Nature Nanotechnology, Nature Publishing Group, vol. 2, pp. 209-215 (Apr. 2007).
Search Report for International Patent Application PCT/IB2010/051317 (Oct. 7, 2010).

* cited by examiner

*Primary Examiner* — Helen Kwok

(57) ABSTRACT

A sensor device for analyzing fluidic samples is provided. The sensor device includes a stacked sensing arrangement having at least three sensing layers and a multilayer structure. The multilayer structure has a hole formed therein which is adapted to let pass the fluidic sample and the stacked sensing arrangement is formed in the multilayer structure in such a way that the fluidic sample passes the stacked sensing arrangement when the fluidic sample passes the hole.

14 Claims, 14 Drawing Sheets

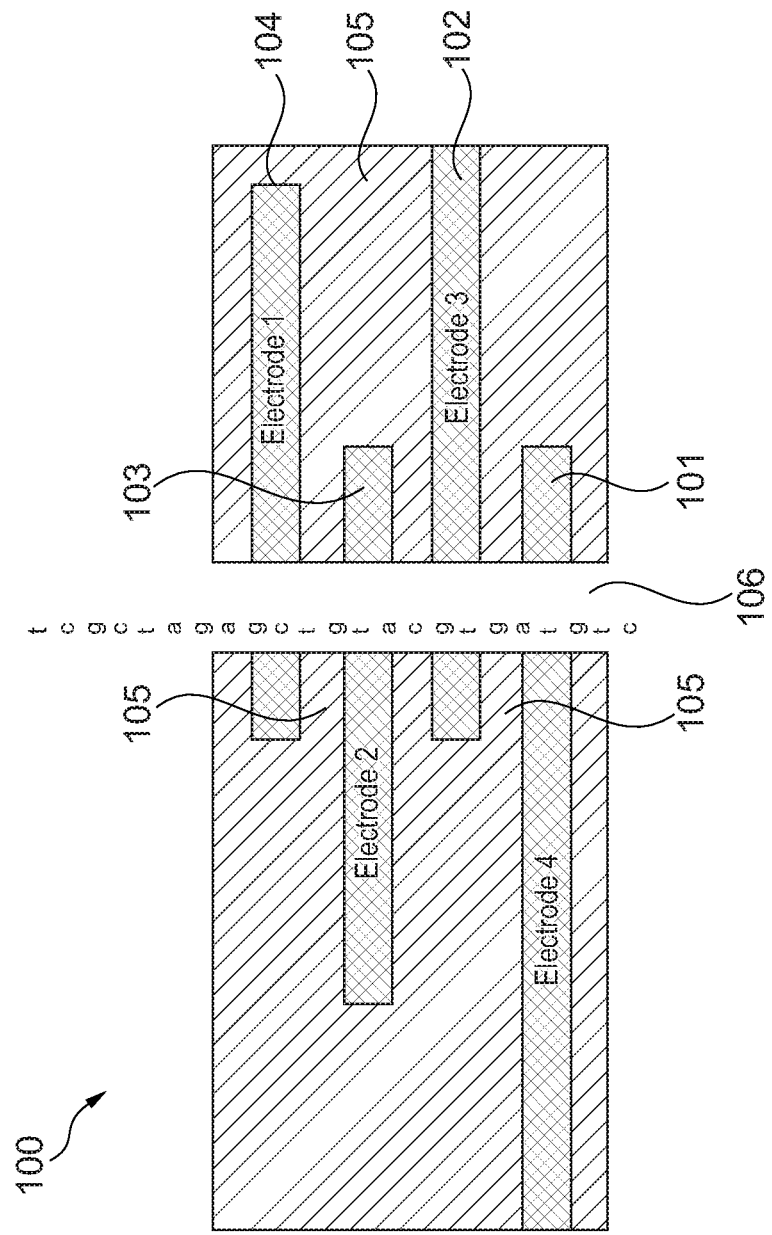

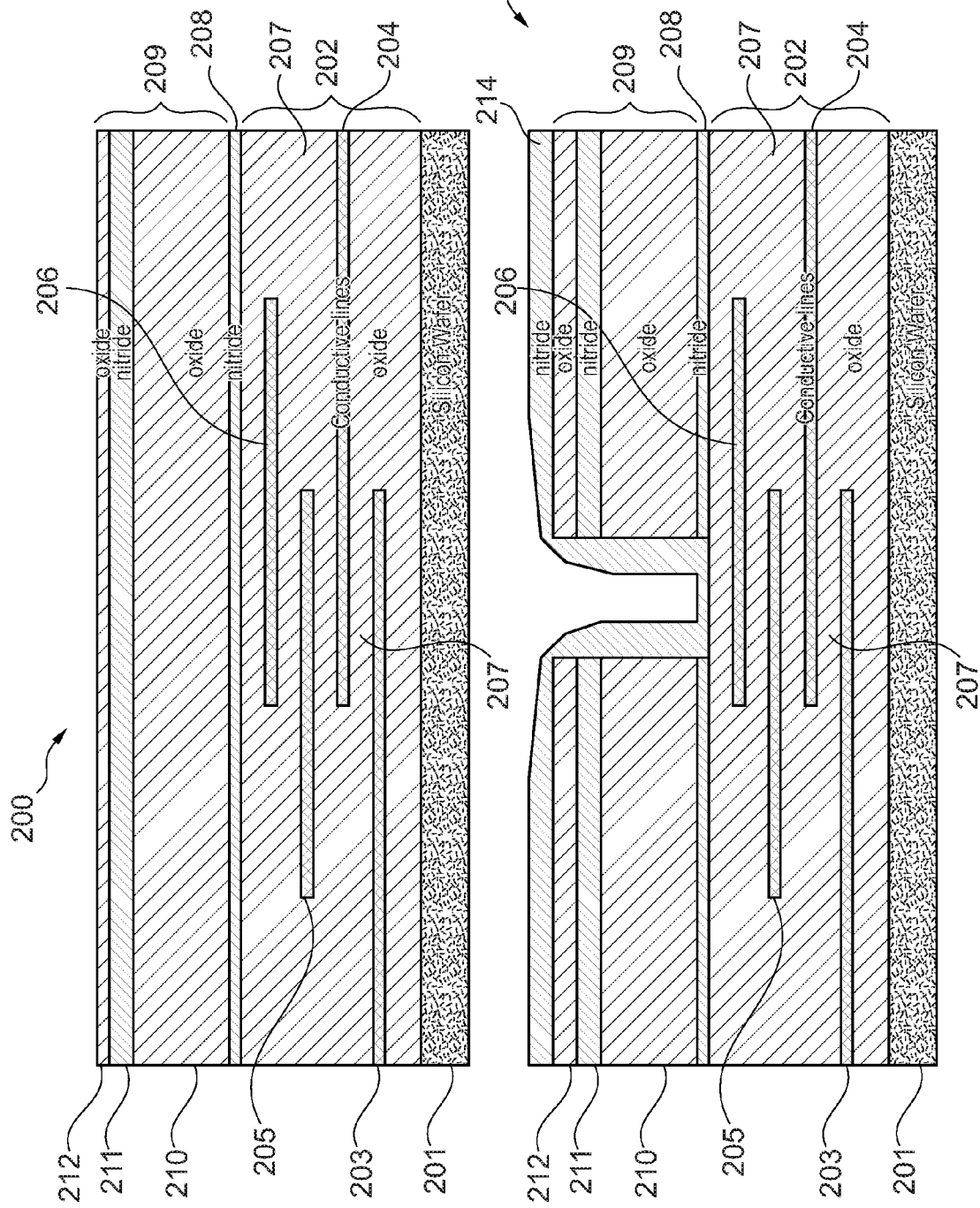

SENSOR DEVICE AND A METHOD OF MANUFACTURING THE SAME

FIELD OF THE INVENTION

The invention relates to a sensor device, in particular to a sensor device for analyzing a fluidic sample.

Moreover, the invention relates to a method of manufacturing a sensor device.

BACKGROUND OF THE INVENTION

A biosensor may be denoted as a device which may be used for the detection of an analyte and may combine a biological component with a physicochemical or physical detector component.

Rapid, reliable and inexpensive characterization of polymers, particularly nucleic acids, has become increasingly important. A high-throughput device that can probe and directly read, at the single-molecule level, hybridization state, base stacking, and sequence of a cell's key biopolymers such as DNA, RNA and even proteins, will dramatically alter the pace of biological development. For example, U.S. Pat. No. 5,795,782 discloses that a voltage bias could drive single-stranded charged polynucleotides through a 1-2 nanometer transmembrane channel in a lipid bilayer. Data in the form of variations in channel ionic current provide insight into the characterization and structure of biopolymers at the molecular and atomic levels. The passage of an individual strand through the channel could be observed as a transient decrease in ionic current. Experiments using biological membranes and pores have demonstrated extraordinary electronic sensitivity to the structure of translocating molecules.

However, conventional methods and devices may still exhibit some problems concerning the reliability of the characterizations or distinguishing different components of a fluidic sample.

OBJECT AND SUMMARY OF THE INVENTION

Thus, there may be a need to provide a sensor device which may more reliable in distinguishing different components or portions of a fluidic sample or analyte, in particular of DNA bases of a DNA strand.

In order to meet the need defined above, a sensor device and a method of manufacturing a sensor device according to the independent claims are provided. Additional enhancements are described in the dependent claims.

According to an exemplary aspect a sensor device for analyzing fluidic samples is provided, wherein the sensor device comprises a stacked sensing arrangement comprising at least three sensing layers and a multilayer structure, wherein the multilayer structure has a hole formed therein which is adapted to let pass the fluidic sample and wherein the stacked sensing arrangement is formed in the multilayer structure in such a way that the fluidic sample passes the stacked sensing arrangement when the fluidic sample passes the hole.

In particular, the hole may be a nanopore having a circular or rectangular cross section, for example. The diameter or width of the nanopore may be less than 20 nm, in particular less than 10 nm, more particularly less than 5 nm, e.g. less than 2 nm. The hole may be a through hole, e.g. a hole passing leading through the whole multilayer structure. Thus, the hole may enable that the fluidic sample, e.g. an analyt, flows through the hole and thus through the multilayer structure. For example, the fluidic sample flowing through the hole may form a separation between two portions of each sensing arrangement, i.e. one portion of each layer of the stacked sensing arrangement may be arranged on one side of the hole while the portion of each layer of the stacked sensing arrangement may be arranged on the opposite side of the hole, e.g. the layers or levels of the stacked sensing arrangement may form a portion of a wall defining the hole, however the portions of each layer of the stacked sensing arrangement may be electrically insulated wherein the hole and/or the fluidic sample may form a part of the electric insulation between the two portions. Additionally, a sealing layer may be provided which forms the sidewalls of the hole and which insulate the stacked sensing arrangement and the fluidic sample passing through the hole from each other.

According to an exemplary aspect a sensor array for analyzing a fluidic sample is provided, wherein the sensor array comprises a plurality of sensor devices according to an exemplary aspect.

In particular, the plurality of sensor devices may be formed in a single multilayer structure comprises a plurality of holes each associated with a respective stacked sensing arrangement.

According to an exemplary aspect a method of manufacturing a stacked sensing arrangement for a sensor device for analyzing components of fluidic sample is provided, wherein the method comprises providing a multilayer structure comprising a stacked sensing arrangement, and forming a hole through the stacked sensing arrangement, wherein the hole is adapted to let pass the fluidic sample. In particular, the forming of the hole may be performed by standard lithography techniques, e.g. etching. However, every suitable method may be used to form said hole, e.g. e-beam, ion-beam or the like. After forming of the hole, the hole may be modified or processed. For example, in some cases the size of the hole may be altered according to the needs. One possible alteration may be to reduce the size by depositing or forming spacers on sidewalls of the hole. In particular, one or more layers of the multilayer structure may form a stopping layer above or below the stacked sensing arrangement, which may be used for further processing steps, e.g. of an etching step or a polishing step. For example, the stacked sensing arrangement may comprise a plurality of sensing layers, i.e. layers which are adapted to measure signal indicative for a specific characteristic of the fluidic sample passing the sensing layer at that point in time. According to a specific embodiment the sensing layer may be a conductive layer.

The term "sensor array" may particularly denote an arrangement of a plurality of sensors or sensor devices for instance in a regular pattern, e.g. a matrix pattern. The number of sensors of such a sensor array may be larger than two, particularly larger than ten, more particularly larger than one hundred.

The term "sensor device" may particularly denote any device which may be used for the detection of a fluidic sample or analyte. Examples for sensors which may be realized according to exemplary embodiments are gas sensors, biosensors, pH sensors, humidity sensors, etc. According to an embodiment, a principle on which the sensor device is based on may be an electric sensor principle which may detect the fluidic sample or particles on the basis of an electric measurement, e.g. by using the stacked sensing arrangement.

The term "fluidic sample" may particularly denote any subset of the phases of matter. Such fluids may include liquids, gases, plasmas and, to some extent, solids, as well as mixtures thereof. Examples for fluidic samples are DNA containing fluids, cells containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc. Furthermore, the fluidic sample may comprise particles, e.g. molecules, organic molecules, biological particles, DNA, RNA, proteins, amino acids, beads, nano-beads, nano-tubes, etc., in particular biological particles, e.g. any particles which play a significant role in biology or in biological or biochemical procedures, such as genes, DNA, RNA, proteins, enzymes, cells, bacteria, virus, etc.

The term "sensing layer" may particularly denote a layer of material able, alone or in combination with other sensing layers, to detect a specific characteristic of the fluidic sample like electric, dielectric, magnetic or optic properties. The sensing layer may be made of conductive material (Ta, TaN, Cu, Al, Ti, . . . ) or a combination of conductive materials. The sensing layer may cover completely or partially the multilayer structure. It may be patterned.

The term "stacked sensing arrangement" may particularly denote an arrangement of several sensing layers, e.g. at least three sensing layers, wherein the sensing layers are arranged above each other and having a dielectric layer arranged in between electrically insulating the sensing layers so that multiple independent sensing arrangements may be formed. The term "above of each other" may particularly denote that the stacked sensing arrangement may have a quasi two-dimensional extension, i.e. the extension in two dimensions is much greater than in the third one, and the sensing layers are stacked or piled up with respect to the third direction, i.e. the direction having the small extension. Each sensing layer may be adapted to perform an independent measurement of a specific characteristic of the passing fluidic sample, wherein the measurement may be based on electric, dielectric, magnetic or optic properties of the fluidic sample or particles in the fluidic sample. A combination of sensing layers may be adapted to perform a measurement of a specific characteristic of the passing fluidic sample, wherein the measurement may be based on electric, dielectric, magnetic or optic properties of the fluidic sample or particles in the fluidic sample.

By providing a sensor device comprising a stacked sensing arrangement it may be possible to perform multiple measurements for one and the same fluidic sample or analyt passing the stacked sensing arrangement. Thus, it may be possible to perform statistical and/or error cancellation treatment afterwards since the fluidic sample, e.g. DNA, may face several sensing layers one after the other in the hole or may face a combination of sensing layers. Furthermore, the use of a stacked sensing arrangement may enable the possibility to arrange the sensing layers close to each other so that a good resolution may be achieved with respect to the different components of the fluidic sample. In particular, an arrangement of the sensing layers may be enabled which provide the possibility that a sequential "reading" or analysis of the fluidic sample may be performed. For example, it may be possible to even distinguish different DNA bases of a DNA strand, when the DNA strand passes through the hole and thus through the stacked sensing arrangement. Additionally the use of a stacked sensing arrangement may enable the implementation of several metal layers or levels in the multilayer structure so that an integrated circuit may be implemented as well in the multilayer structure. For example, it may be possible to integrate electronic components into the multilayer structure, e.g. an on-chip amplification or an on-chip signal processing may be possible.

Additionally, the provision of a sensor array comprising a plurality of sensor devices may lead to an increasing parallelization of sensing or analyzing the fluidic sample. Optionally, the sensor device or sensor array may be arranged on or in a substrate which may form support for the sensor device or sensor array and/or which may also support or implement integrated circuitry adapted to perform some of the measurements or processing of the signals induced or caused by the passing fluidic sample.

Next, further exemplary embodiments of the sensor device will be explained. However, these embodiments also apply to the sensor array and to the method of manufacturing a stacked sensing arrangement for the sensor device.

According to an exemplary embodiment of the sensor device the stacked sensing arrangement is formed by a stack of sensing layers.

Thus, the term "stack of sensing layers" may particularly denote an arrangement of at least three sensing layers, wherein the sensing layers are arranged above each other and having a dielectric layer arranged in between electrically insulating sensing layers so that a capacity or capacitor may be formed by two sensing layers, The term "above of each other" may particularly denote that the stack of sensing layers may have a quasi two-dimensional extension. All of the sensing layers may have the same size or may have different sizes.

A sensing layer may be a part of several capacitors, for example it may be form a capacitor with the sensing layer just above and a capacitor with the sensing layer just below.

By providing a sensor device comprising a stack of sensing layer it may be possible to perform multiple measurements for one and the same fluidic sample or analyt passing the plurality of capacities. For measuring a signal associated with the passing of the fluidic sample a voltage change in the sensing layers, an impedance measurement between two sensing layers and/or a current due to tunnelling or resonant tunnelling between two sensing layers may be measured. Furthermore, the use of a stack of sensing layers may enable the possibility to arrange the sensing layer close to each other so that a good resolution may be achieved with respect to the different components of the fluidic sample. In particular, an arrangement of the sensing layers may be enabled which provide the possibility that a sequential "reading" or analysis of the fluidic sample may be performed. For example, it may be possible to even distinguish different DNA bases of a DNA strand, when the DNA strand passes through the hole and thus through the stacked sensing arrangement.

According to an exemplary embodiment of the sensor device the stack of sensing layers comprises at least three sensing layers which are arranged above of each other and which are electrically insulated from each other by a dielectric layer arranged between the sensing layers. In particular, the stack of sensing layers may be planar, i.e. a layered structure having substantially a two dimensional extension, i.e. having relatively large directions in two dimensions while in the third dimension, e.g. the thickness, the extension is small compared to the other two dimensions, e.g. the thickness may be less than the a tenth or even less than one percent of the extensions of the width and/or the length of the stack of sensing layers.

According to an exemplary embodiment of the sensor device the sensing layers have a thickness of less than 10 nm. In particular, the thickness may be less than 5 nm or even less than 2 nm. Preferably, the thickness may be less than 1 nm, e.g. in the range between 0.1 nm and 0.5 nm.

According to an exemplary embodiment of the sensor device the thickness of the dielectric layer is less than 10 nm. In particular, the thickness of the dielectric layer may be less than 5 nm or even less than 3 nm. Preferably, the thickness or the dielectric layer may be less than 1 nm.

By providing sensing layers and/or dielectric layer between sensing layers of different layers having such a small thickness it may be possible to analyze or distinguish very small or short components, parts or portions in the fluidic sample or of particles in the fluidic sample. For example, in case the fluidic sample comprises a DNA strand it may be possible that even single bases may be distinguished from each other.

According to an exemplary embodiment of the sensor device the thickness of the dielectric layer is less than 10 nm. In particular, the thickness of the dielectric layer may be less than 5 nm or even less than 3 nm. Preferably, the thickness or the dielectric layer may be less than 1 nm.

According to an exemplary embodiment the sensor device further comprises an integrated circuit arrangement coupled to the sensing layers of the stacked sensing arrangement.

In particular, the integrated circuit arrangement may be included in the multilayer structure or may be formed as a part of the multilayer structure. For example, the integrated circuit arrangement may comprise electronic components like transistors, memories, processors, or the like, which may be implemented by known semiconductor technologies, e.g. by CMOS technology. The integrated circuit arrangement may form part of a detection system for detecting components of the fluidic sample or analyt and may even include processors or part thereof for processing the signals sensed by using the stacked sensing arrangement. Furthermore, the integrated circuit arrangement may include some amplifier which may also be formed in CMOS technology and which may be adapted to provide amplification for the signals provided by the stacked sensing arrangement.

According to an exemplary embodiment of the sensor device at least one of the sensing layers is adapted to actuate the fluidic sample.

Next, further exemplary embodiments of the method of manufacturing a stacked sensing arrangement for a sensor device sensor device will be explained. However, these embodiments also apply to the sensor device and to the sensor array.

According to an exemplary embodiment of the method the multilayer structure comprises a cover layer covering the stacked sensing arrangement. In particular, the cover layer may comprise a plurality of sublayers, which may be formed by dielectric material, e.g. silicon nitride or silicon oxide.

According to an exemplary embodiment the method further comprises forming a primary hole trough the cover layer, wherein the primary hole has a first size. In particular, the primary hole may be formed by using lithographic techniques, and etching processes.

According to an exemplary embodiment the method further comprises narrowing the primary hole by forming a spacer arrangement on sidewalls of the primary hole.

By narrowing the primary hole a hole having a second size may be formed wherein the second size is smaller than the first size. This narrowing may be performed by any known deposition step, e.g. by chemical vapour deposition or the like. By such a narrowing it may be possible to form a hole having a smaller size, diameter or dimension than it is possible to achieve by standard lithography techniques since the deposition step may be a suitable method to form layers of precise thickness, which may be used as spacers so that an accurate dimension of the primary hole may be adjustable. Since deposition techniques are well known and precise it may thus be possible to form very small holes or nanopores. In particular, the size, diameter or width of the unnarrowed hole may be in the range of 20 nm or even more than 20 nm while the size of the narrowed hole may be in the range between 1 nm and 10 nm, or even below. To provide holes or nanopores having a such a small diameter may be advantageous for fluidic samples including small particles or the like, e.g. DNA strands, since less other material of the fluidic sample may be present in the sensing area of the sensing layers, so that a shielding effect of the other material may be reduced. In particular, in case of DNA strands the small dimension of the nanopore may also lead to a stretching of the DNA strand so that an improved measurement may be possible.

The term "spacer" may particularly denote a layer or a structure formed mainly in the vertical direction on another structure. It may be formed by isotropic deposition of material on a vertical structure. It may be used to increase the horizontal dimension of a multilayer structure surrounding a hole and therefore narrowing the hole.

The technique of narrowing the hole with spacer may be an advantage to etch through a multilayer structure comprising a large number of layers.

According to an exemplary embodiment of the method the hole in the stacked sensing arrangement is formed by utilizing the primary hole. In particular, the narrowed primary hole may be used, e.g. the primary hole may be used as an etching mask. Thus, a small hole may be achievable by using the primary hole or the narrowed primary hole as an etching mask.

According to an exemplary embodiment of the method the multilayer structure is provided on a substrate. In particular, the substrate may include an integrated circuit arrangement which may be formed by standard semiconductor technologies or processing, e.g. CMOS technology. The formation or manufacturing of the substrate may form a part of the described exemplary embodiment of the invention or the substrate may be a pre-fabricated or standard substrate which may be provided by a supplier.

According to an exemplary embodiment the method further comprises forming contact terminals adapted to contact the stacked sensing arrangement.

According to an exemplary embodiment the method further comprises integrating electronic elements in the multilayer structure.

Summarizing according to a specific exemplary aspect a sensor device or sensor arrangement may be provided which comprises a plurality of stack of sensing layers of at least three sensing layers, each combined stacked sensing arrangement with one hole through which a fluidic sample or analyt may pass. The hole may also be called a nanopore. The stack of sensing layers may be formed on or in a substrate and the plurality of holes may be through holes (or through drilling or clearance holes or via holes). Thus, a plurality of through holes may be formed to extend through the entire substrate which through holes may comprise side walls but may be free of a closed bottom. Each of the plurality of stack of sensing layers may be used to measure an electric signal indicative for the fluidic sample or at least a portion or part of the fluidic sample passing through the respective hole at that point in time. The sensing layers may have a small thickness, i.e. may be thin, so that components of the fluidic example may be distinguishable with good resolution. For example, the fluidic sample may comprise DNA strands which are analysed by the sensor devices or a sensor array comprising a plurality of sensor devices, while the fluidic sample flews through the holes of the sensor array. In case the distance between the different sensing layers of each stack of sensing layers is small enough it may be possible to identify the sequence of the DNA bases. However, the multiple measurements and thus the redundancy of measurements during the passing of the fluidic sample through the whole stacked sensing arrangement may at least improve the achievable resolution of the analysis. In this context it should be noted that this redundancy of measurements may not only be achievable by using at least three sensing layers based on the same detection principle but may also be achievable by using a stacked sensing arrangement, in which several layers of sensing elements or sensing units based on different detection principles electric, magnetic or optic principles. Each of the sensing layers may be adapted to measure a characteristic which may be evaluated by a respective processing element. Such a processing element may already formed in or on the substrate and may perform a complete processing or may perform a preprocessing the result of which may be transmitted to an external entity, e.g. an external processor or CPU of a computing device. For the transmission a communication interface may be provided, particularly a Universal Serial Bus (USB) interface, electrically coupled to the sensing layers or to a processing element. Thus, signal may be supplied to a coupled entity such as a communication partner device. Such a communication partner device may be a computer (such as a laptop) at which the measurements may be further evaluated. In an alternative embodiment, the sensor array may be completely self-sufficient so that no coupling with an external entity is necessary. However, in an embodiment in which a communication interface is present, the coupled entity such as a personal computer may further process the measurements and/or display them to a user via a GUI (Graphical User Interface). The communication between the sensor array and the communication partner device may be a wired connection (such as in an embodiment with a USB interface), or may be a wireless communication (for instance using Bluetooth, infrared communication or radio frequency communication).

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Polishing may include CMP (chemical mechanical polishing). Removing layers or components may include etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

Any process technologies like CMOS, BIPOLAR, BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 1 schematically illustrates a stacked sensing arrangement.

FIG. 2A to 2D schematically illustrates a method of manufacturing a sensor device, in particular of a nanopore of the sensor device.

DESCRIPTION OF EMBODIMENTS

Figure 2C:
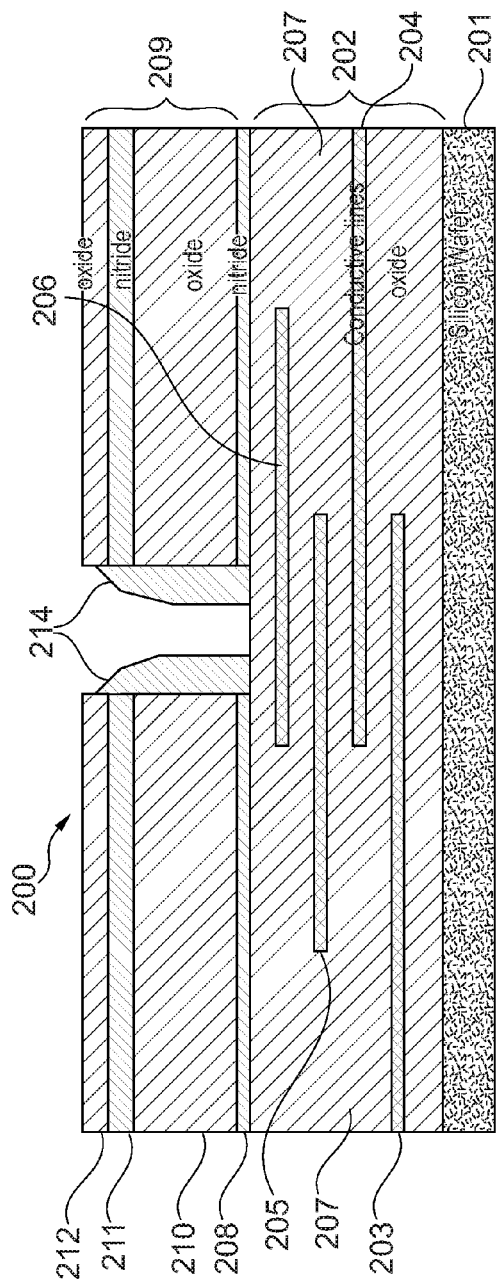

The illustration in the drawing is schematical. In different drawings, similar or identical elements are provided with the same or similar reference signs.

FIG. 1 schematically illustrates a stacked sensing arrangement 100 comprising four sensing layers 101, 102, 103, and 104 which are insulated from each other, e.g. by a dielectric layer, e.g. a silicon oxide layer 105. The insulation may be formed by a single layer or may be formed by several independent layers or sublayers. In particular, all sublayers or the whole insulation may be formed of or may at least comprise a same material, e.g. silicon oxide. Furthermore, the stacked sensing arrangement 100 comprises a hole or nanopore 106, which passes through all of the sensing layers and the dielectric layer, i.e. may form a through hole 106. Therefore, a fluidic sample, e.g. a fluid comprising particles like DNA strands, which is schematically indicated by the respective bases marked with the letters depicted in FIG. 1, may flow through the nanopore while passing the stacked sensing arrangement 100. The stack of sensing layers may be formed by known lithographic techniques which will be described in more detail with respect to FIG. 2. When the fluidic sample passes through the stack of sensing layers a change of electrical characteristics of the sensing layers may form a signal which may be transmitted from the sensing layers to an electric circuitry, wherein the signal may depend on the bases just passing the respective sensing layers.

In the following, referring to FIG. 2, a method of manufacturing a sensor device, in particular of a nanopore of the sensor device is described. FIG. 2A shows a multilayer structure 200 comprising a substrate 201 on which a stack of sensing layers 202 is formed comprising four sensing layers 203, 204, 205, and 206 which are formed by electrical conductive material, e.g. TaN, Cu, Al or the like. The sensing layers may have different sizes or extension in the width and length dimension, so that each single layer may be contacted from above (in the coordinate system of FIG. 2) without interfering with each other. The sensing layers are separated by a dielectric layer 207. Preferably, the material of the dielectric layer 207 is one which has a low probability to trap charges, e.g. silicon oxide. On top of the stack of sensing layers 202 a further dielectric layer 208 is formed which may be used afterwards a stopping layer, e.g. for an etching process. The stopping layer 208 may comprise silicon nitride. On top of the stopping layer a cover layer 209 is formed which may comprise several sublayers 210, 211, 212 as shown in FIG. 2A and which may be formed of or at least comprising different dielectric materials, e.g. silicon oxide and silicon nitride. The dielectric layer 208 is preferentially made of silicon nitride. The dielectric layer 210 is preferentially made of silicon oxide. The dielectric layer 211 is preferentially made of silicon nitride. The dielectric layer 212 is preferentially made of silicon oxide.

For forming the different layers of the multilayer structure 200 known deposition, lithography and etching techniques may be used. Preferably, the thickness of the sensing layers and the dielectric layer 207 in between are as thin as possible, in order to achieve an improved resolution with respect to the fluidic sample, e.g. to differentiate different base pairs of a DNA strand.

FIG. 2B schematically shows the multilayer structure 200 of FIG. 2A after a primary hole is formed in the cover layer 209 which is then partially filled by a spacer layer 214, in order to achieve a hole having a small size or diameter. Thus, preferably the etching is performed by an etching process already enable a minimal size of the etched hole. The etching may use the stopping layer 208 as an etch stop. Furthermore, the spacer layer 214 or the spacer reduces the size of the primary hole and narrows the same. The spacer layer may be formed by isotropic deposition a dielectric material, e.g. silicon nitride.

FIG. 2C schematically shows the multilayer structure of FIG. 2B after partially removing the spacer layer 214 in order to form spacer in the primary hole. Preferably, the etching is a selective etching, e.g. by using a selective etching agent. For example, in case the spacer layer is formed by silicon nitride the etching agent may etch silicon nitride well but may etch silicon oxide only to a small extend. This etching step may be particularly performed in order to remove the stopping layer 207 on the bottom of the primary hole.

Figure 2D:
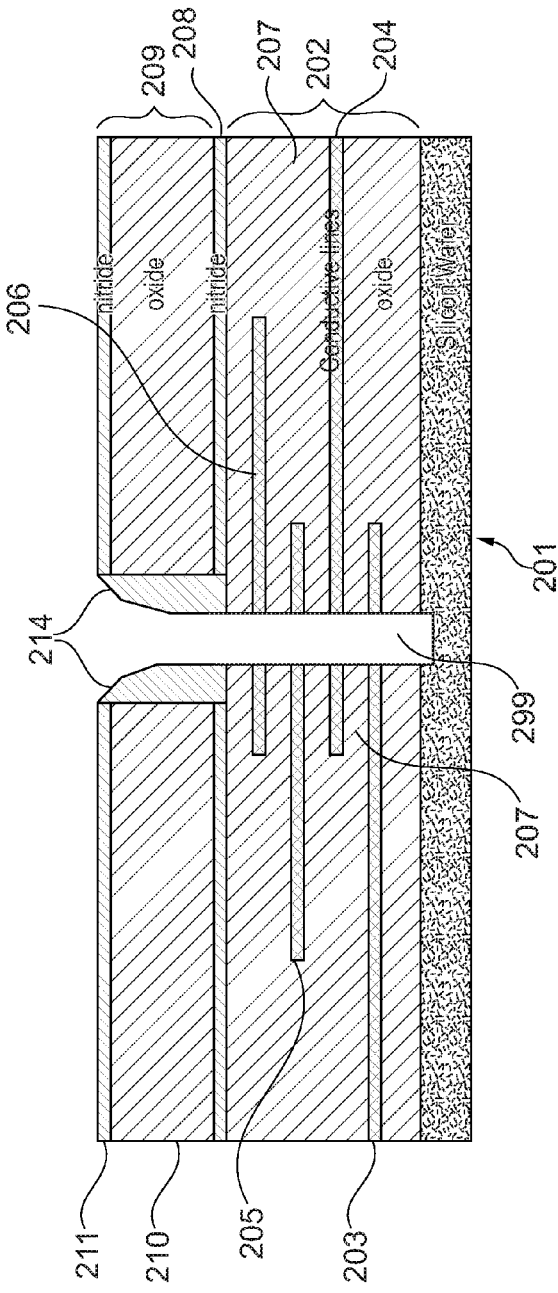

FIG. 2D schematically shows the multilayer structure 200 of FIG. 2C after a further etching step which is performed to etch a hole or nanopore 299 into the stack of sensing layers 202. Thus, an etching agent may be used which is as much as possible selective with respect to silicon nitride, i.e. may etch silicon oxide well but etch silicon nitride only to a small extend, in order to save some of the spacer 214. However, in case the spacers are formed of another material the etching agent is preferably selective with respect to this material. The etching step uncovers the portions of the substrate 201 on the bottom of the formed nanopore 299.

Figure 3A:
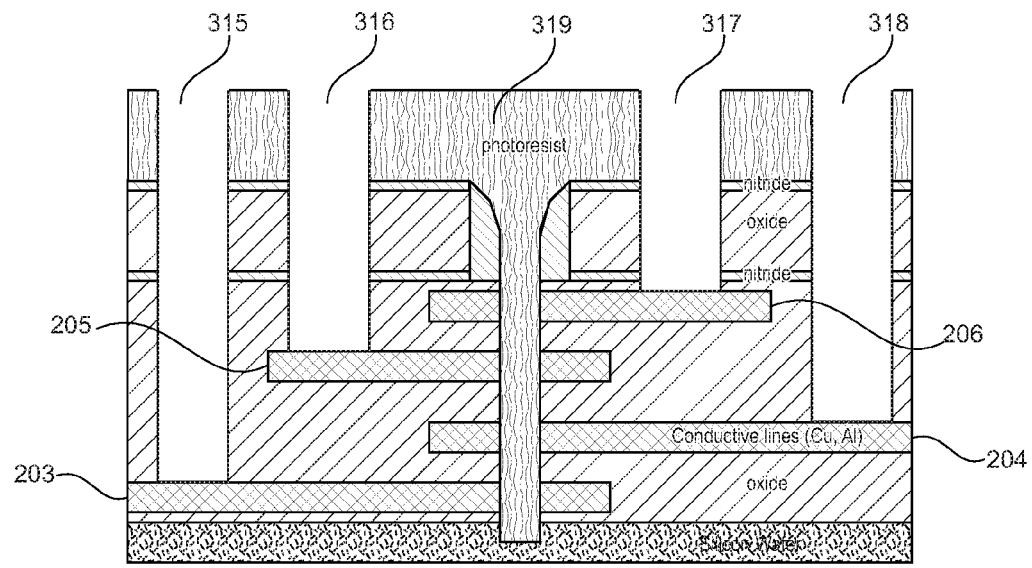
FIG. 3A to 3B schematically illustrates a first method of connecting a sensor device.

In the following, referring to FIG. 3, a first method of connecting a multilayer structure or a sensor device, which may be formed by the process described with respect to FIG. 2, is described. In a first step vias 315, 316, 317, and 318 are formed to uncover portions of the sensing layers 203, 204, 205, and 206, respectively. For the via forming step a further etching step may be performed which may include the deposition and patterning of a photoresist layer 319. Since the sensing layers have different extensions in the lateral dimension in FIG. 3 it is possible to contact each sensing layer independently as shown in FIG. 3. Alternatively, to forming the sensing layers so that they have different extensions additionally conductive lines may be included in the multilayer structure enlarging the dimensions of the sensing layers. In FIG. 3A the conductive lines are not shown since they are only an extension of the sensing layers. The conductive layers may be formed by Cu or Al.

Figure 3B:
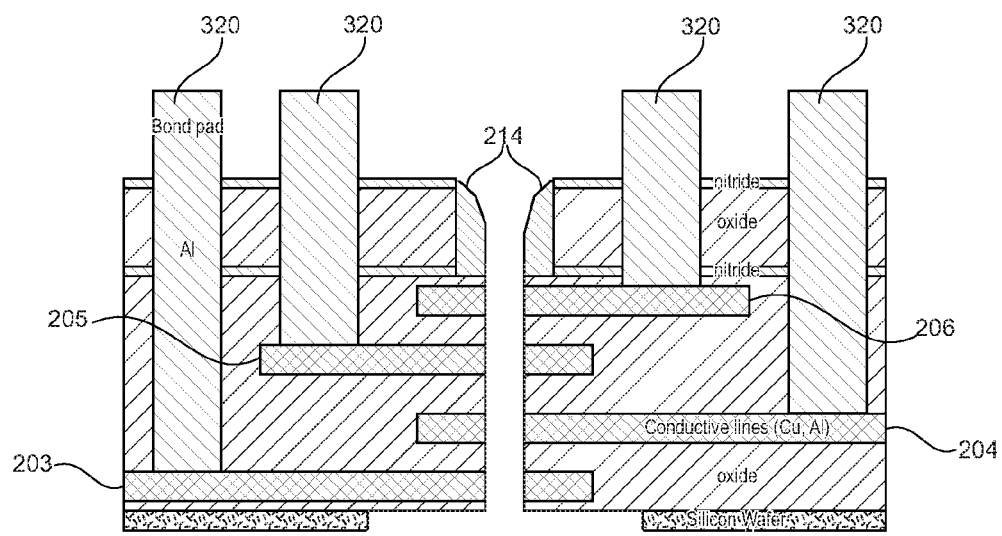

FIG. 3B shows the multilayer structure of FIG. 3B after a deposition of the vias are filled with conductive material, e.g. Al, so that contact lines 320 are formed. Afterwards the photoresist 319 is stripped leaving contact or bond pads of the conductive material. Afterwards, the substrate is removed, e.g. by backgrinding and/or chemical etching.

The connecting method described in the context of FIG. 3 may be particular suitable in case the sensing layers have a thickness which ensures that the conductance is high enough that no voltage drop occurs in the sensing layers.

In the following, referring to FIG. 4, a second method of connecting a multilayer structure or a sensor device, which may be formed by the process described with respect to FIG. 2, is described. For clarity reasons only some of the reference signs which are already discussed and described in context to FIG. 2 are shown in FIG. 4. A sacrificial layer 430 and an optional hardmask 431 is deposited on top of the multilayer structure of FIG. 2 for further processing. Possible materials for the sacrificial layer may be a polymeric material or polysilicon. The sacrificial layer and the optional hardmask are then patterned, e.g. by etching, in such a way that the hole is filled and covered by the sacrificial layer and the hardmask.

Figure 4A:
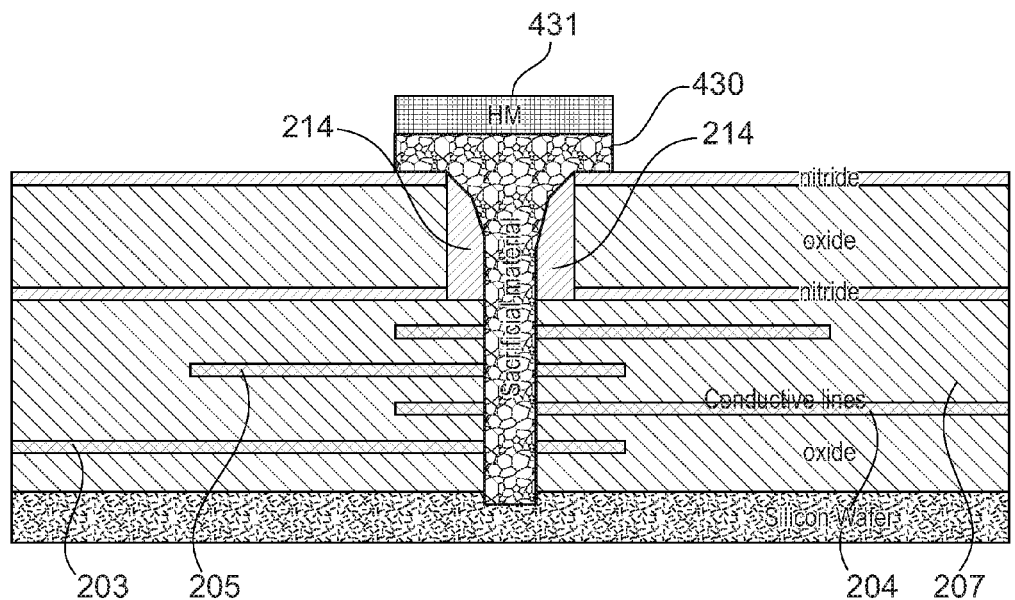
FIG. 4A to 4J schematically illustrates a second method of connecting a sensor device.
Figure 4B:
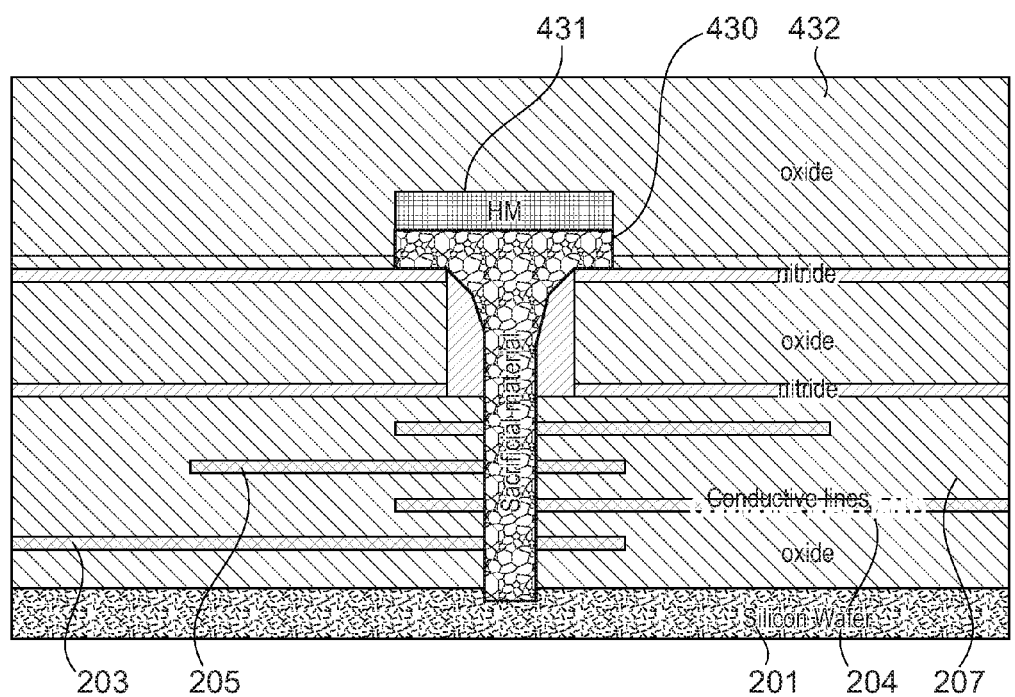

FIG. 4B shows the multilayer structure of FIG. 4A after deposition of a top layer 432, which may be formed by a dielectric material, e.g. silicon oxide. The top surface of the top layer 432 may then be planarized, e.g. by chemical mechanical polishing (CMP).

Figure 4C:
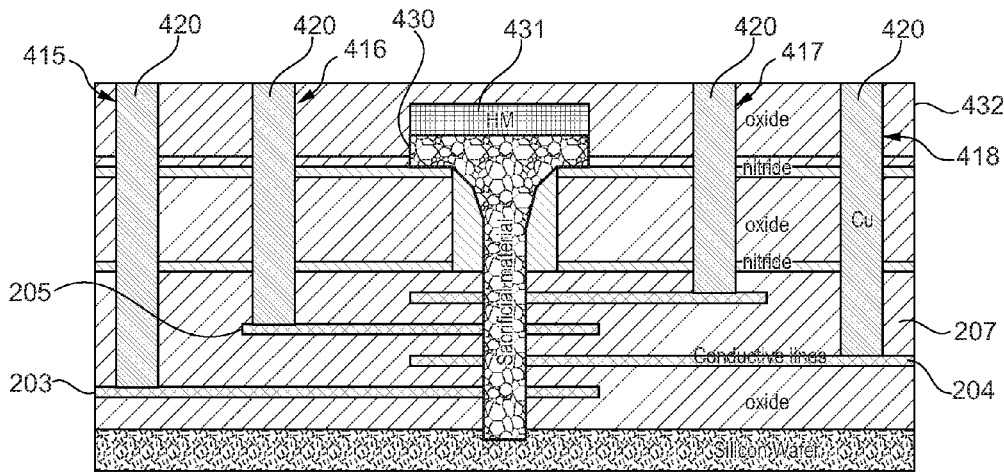

FIG. 4C shows the multilayer structure of FIG. 4B after a further etching step to form vias 415, 416, 417, and 418 which may be used to contact the sensing layers by contact lines 420, which may be formed by plugs of metallic material, e.g. Cu, W or other suitable materials. For the respective etching step the sensing layers, which may be formed by TaN, may be function as stopping layers. After the deposition of the contact lines the surface may be planarized again, e.g. by CMP, in order to planarized the plug material.

Figure 4D:
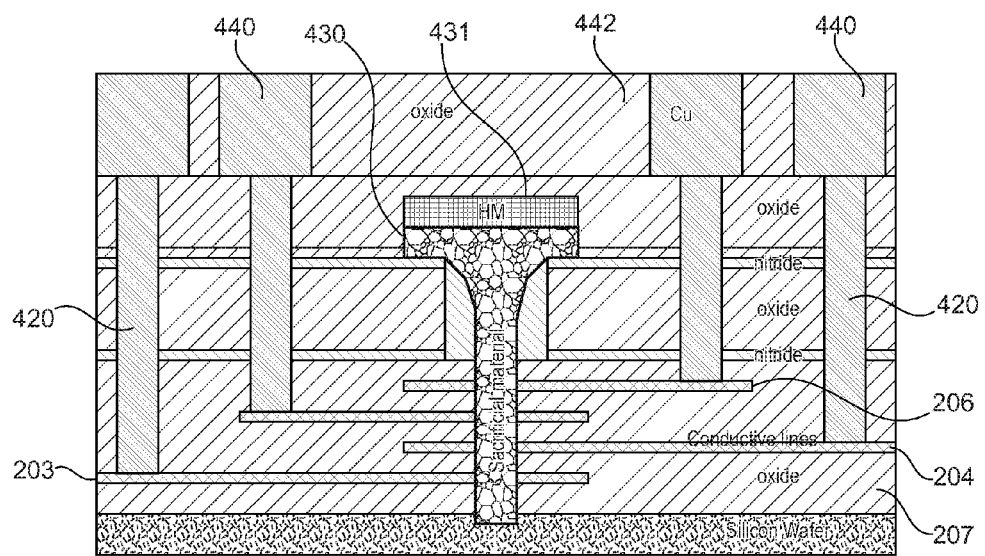
Figure 4E:
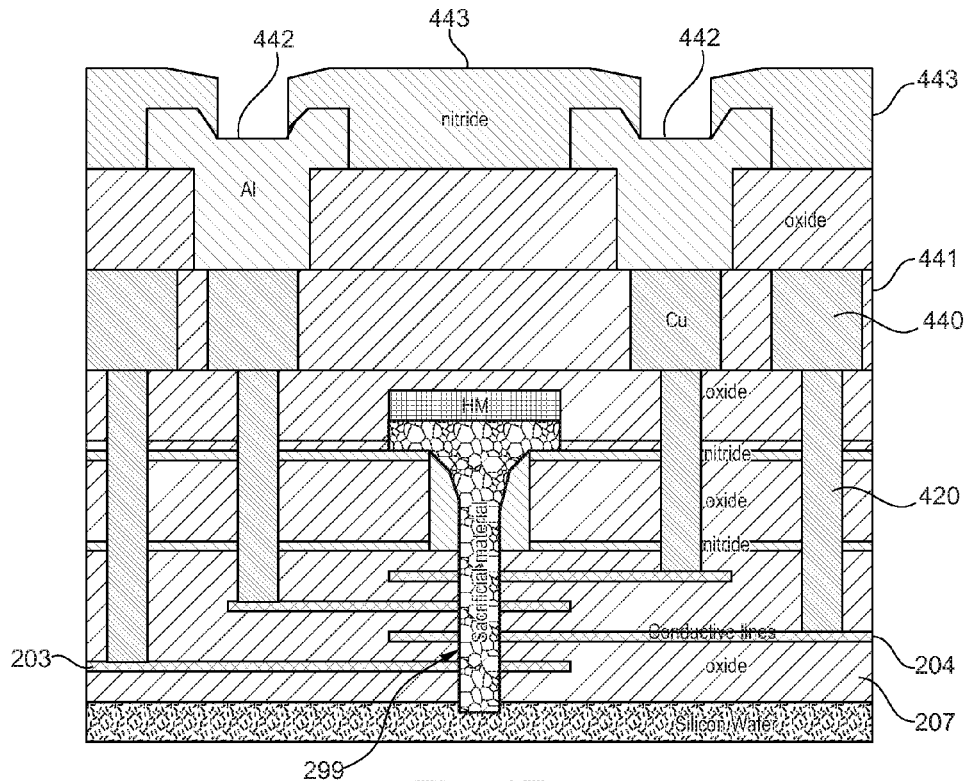

FIG. 4D and FIG. 4E show the multilayer structure of FIG. 4C after some optional further processing steps for forming additional metal levels or metal layers 440 (e.g. Cu), dielectric layers 441 (e.g. silicon oxide), bond pads 442 (e.g. Al), and passivation layers 443 (e.g. silicon nitride), and the like by using deposition steps, etching steps and/or CMP steps. In FIG. 4E only the bond pads for two sensing layers are shown for the sake of clarity. Additionally, the bond pads for the sensing layers may be formed on different levels or planes.

Figure 4F:
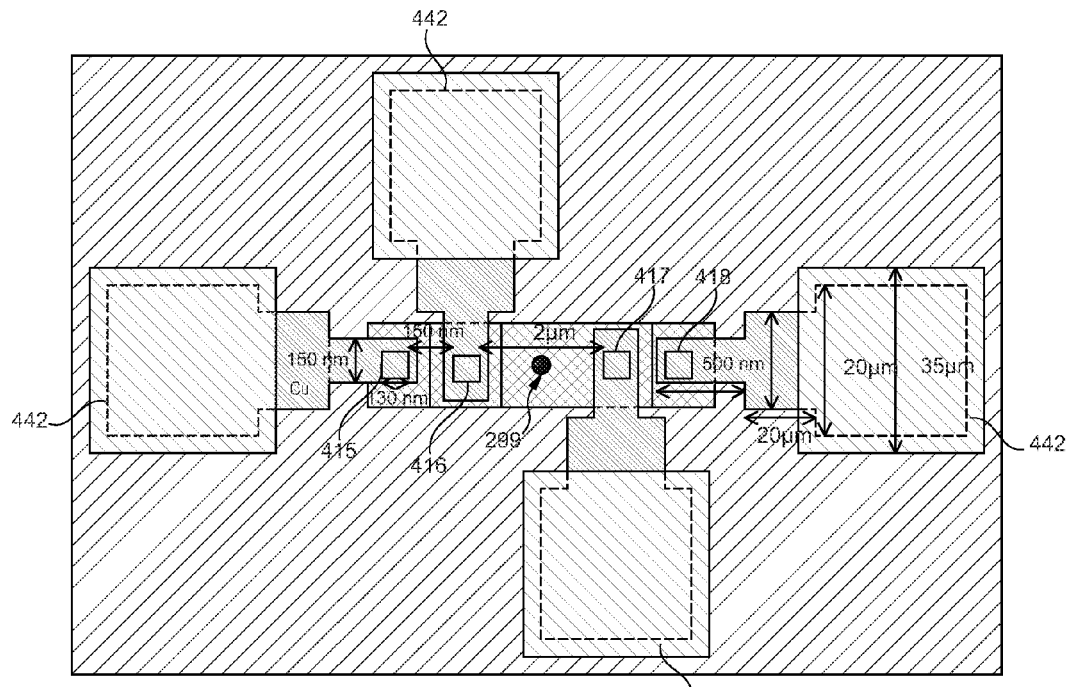

FIG. 4F shows the multilayer structure of FIG. 4E in a top view. Additionally, some dimensions of the different elements are shown. However, it must be clearly stated that the dimensions are not limited to the given numbers but may be adapted to the specific needs. In particular, the dimensions of the bond pads 442 are shown which may have a rectangular or square cross section and a size of about 20 micrometer to 35 micrometer. Furthermore, the four vias 415, 416, 417, and 418 can be seen in FIG. 4F and may have a size of about 130 nm and a distance of about 150 nm to 2 micrometer from each other. Moreover, the filled nanopore 299 formed in the multilayer structure.

Figure 4G:
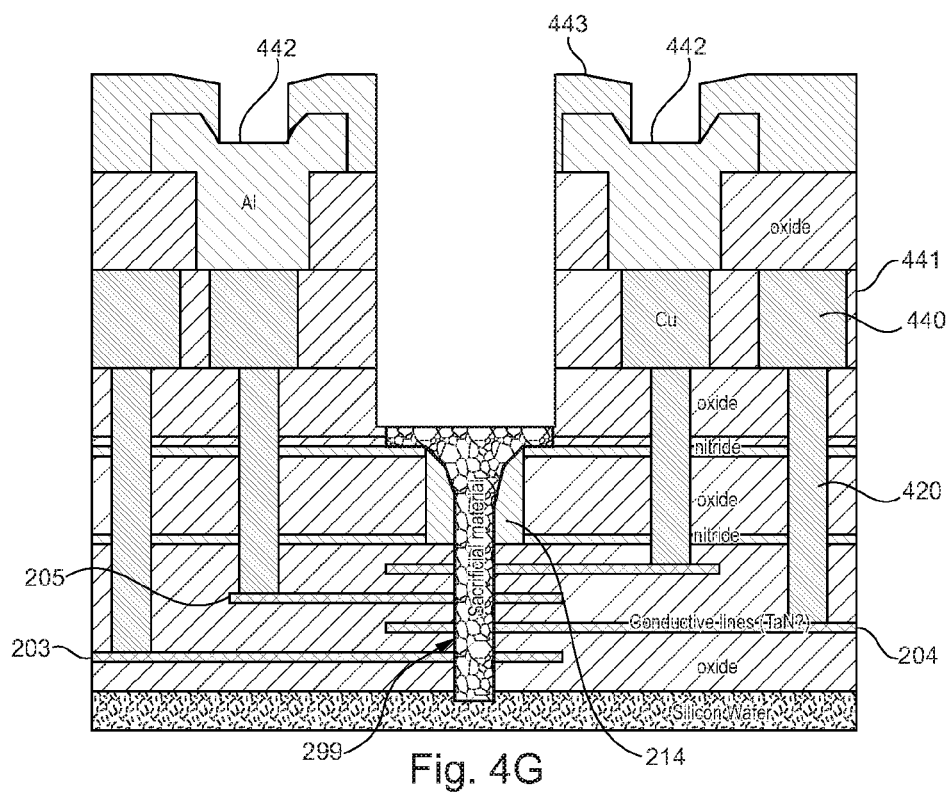

FIG. 4G shows the multilayer structure of FIG. 4E after an additional etching step performed in order to uncover the sacrificial layer 430 or the hardmask 431 by patterning the passivation layer 443 and the dielectric layer 441. Preferably an etching agent may be used which is selective with respect to the material of the sacrificial layer 430, i.e. which ensures that the sacrificial layer 430 is not etched or at least only etched to a small extend.

Figure 4H:
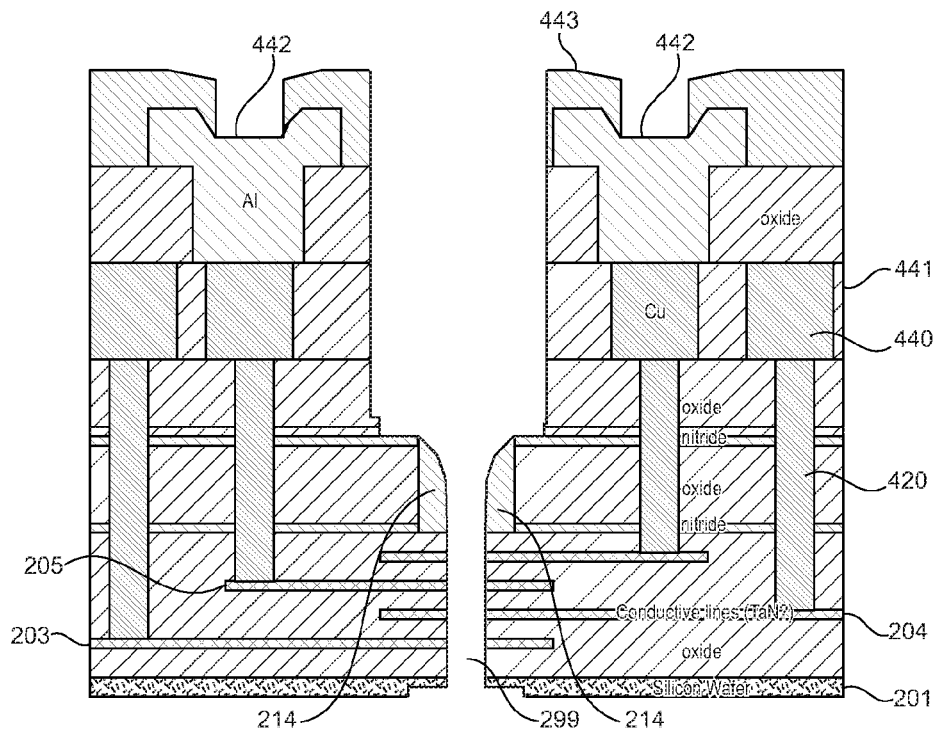

FIG. 4H shows the multilayer structure of FIG. 4G after an additional etching step which is performed in order to remove the sacrificial layer 430. In this case the agent may be selected that only or at least primarily the sacrificial layer 430 is removed, so that the substrate, e.g. a silicon wafer, is uncovered in the area of the nanopore 299. Afterwards the substrate is processed to remove it at least partially. This processing may be performed by backgrinding or etching.

Figure 4I:
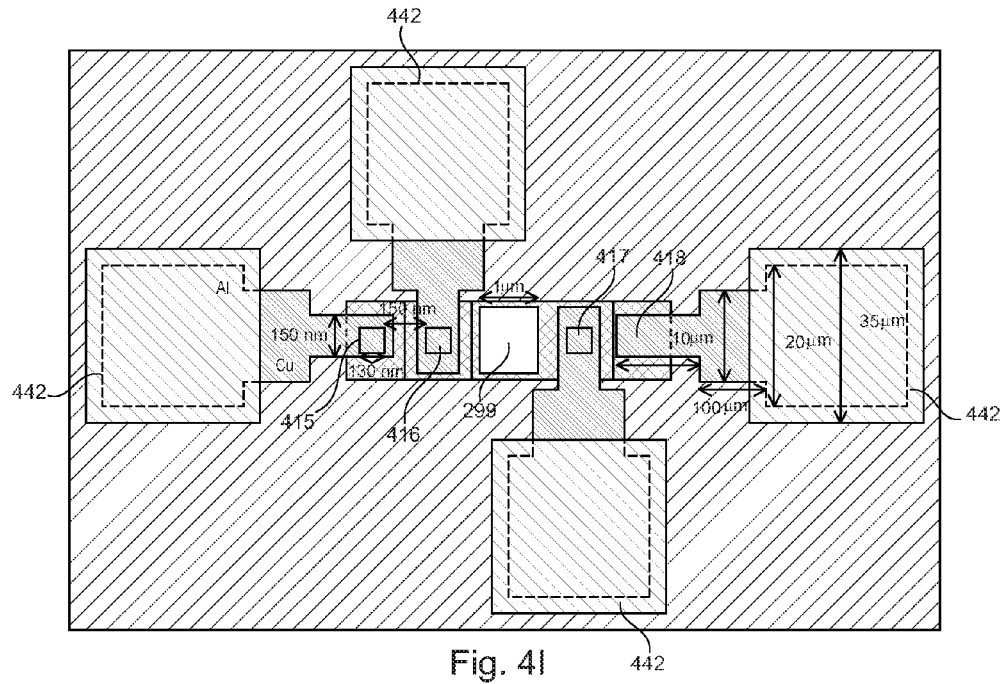

FIG. 4I shows the multilayer structure of FIG. 4H in a top view. The FIG. 4I differs from FIG. 4F mainly in the fact that the nanopore 299 is not filled with the sacrificial layer any more.

Figure 4J:
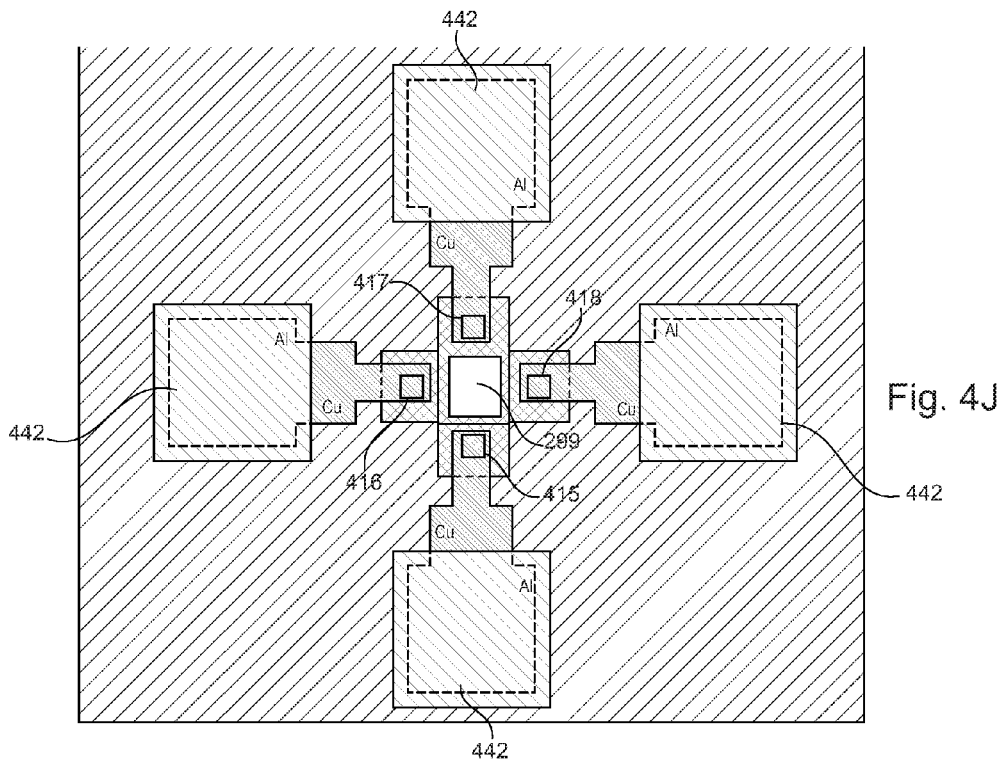

FIG. 4J shows the multilayer structure of FIG. 4I in another alternative arrangement. In particular, the sensing layers are formed in a way that each sensing layer extends mainly in a different direction. For example, in the case of FIG. 4 showing a stack of sensing layers comprising four sensing layers, the sensing layers may extend substantially in directions differing by an angle of 90°. Such an arrangement may enable the use of shorter sensing layers which may improve a measurement performed by using the sensing layers, e.g. by reduce parasitic capacities and resistance of the stack of sensing layers and the multilayer structure.

Figure 5A:
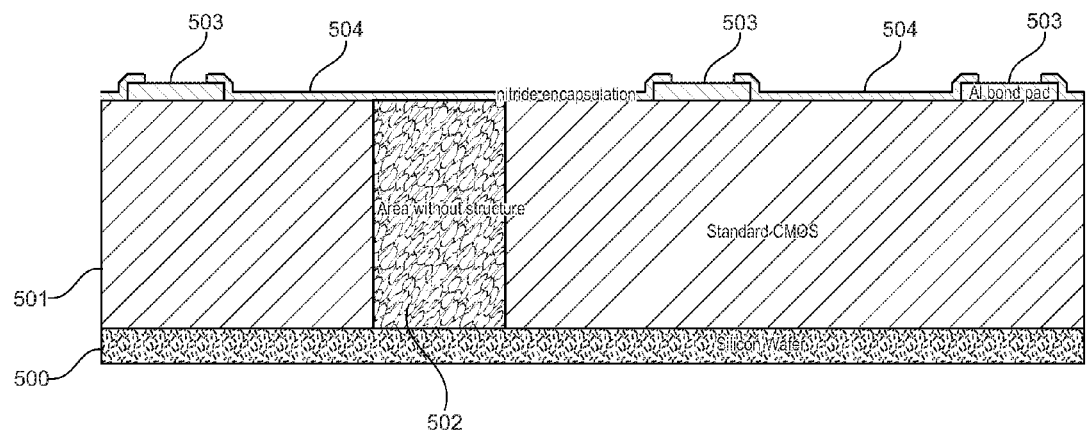
FIG. 5A to 5I schematically illustrates a third method of connecting a sensor device.

In the following, referring to FIG. 5, a third method of connecting a multilayer structure or a sensor device, which may be formed by the process described with respect to FIG. 2, is described. FIG. 5A shows a substrate 500 onto which integrated circuitry is formed which is depicted only schematically in FIG. 5 by the layer 501. The integrated circuitry may be formed by using known or standard techniques, e.g. CMOS and may form an integrated chip. A specific area 502 of the substrate may comprise no structure of integrated circuitry. In this area afterwards a nanopore of a sensor device may be formed. On top of the layer 501 some bond pads 503 are indicated in FIG. 5A which may be formed by conductive material, e.g. Al. Furthermore, FIG. 5A shows an encapsulation layer 504 which is formed by a dielectric material, e.g. silicon nitride. Above the bond pads 503 the encapsulation may be removed in order to uncover the bond pads. The integrated chip may be a standard chip and may be commercially available or may be manufactured according to specific needs.

Figure 5B:
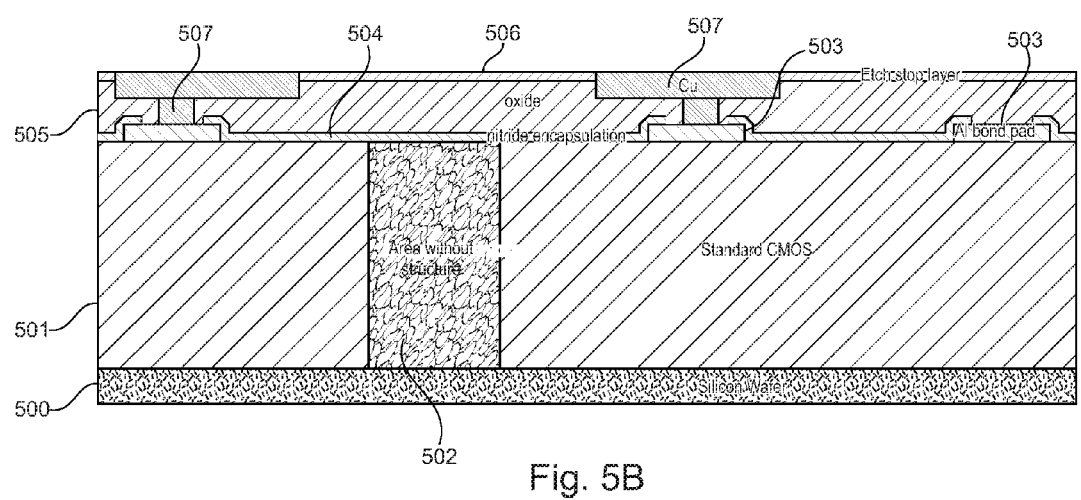

FIG. 5B shows the multilayer structure of FIG. 5A after some further processing steps, in which a dielectric layer 505, e.g. silicon oxide, is formed on the structure which is afterwards planarized, e.g. by CMP. Further, a etch stop layer 506 is deposited on the dielectric layer 505 which may be patterned afterwards to provide access to at least some of the bond pads 503, so that the uncovered bond pads may be contacted by a metal level or layer 507 which may be formed by a metallic layer, e.g. a Cu layer.

Figure 5C:
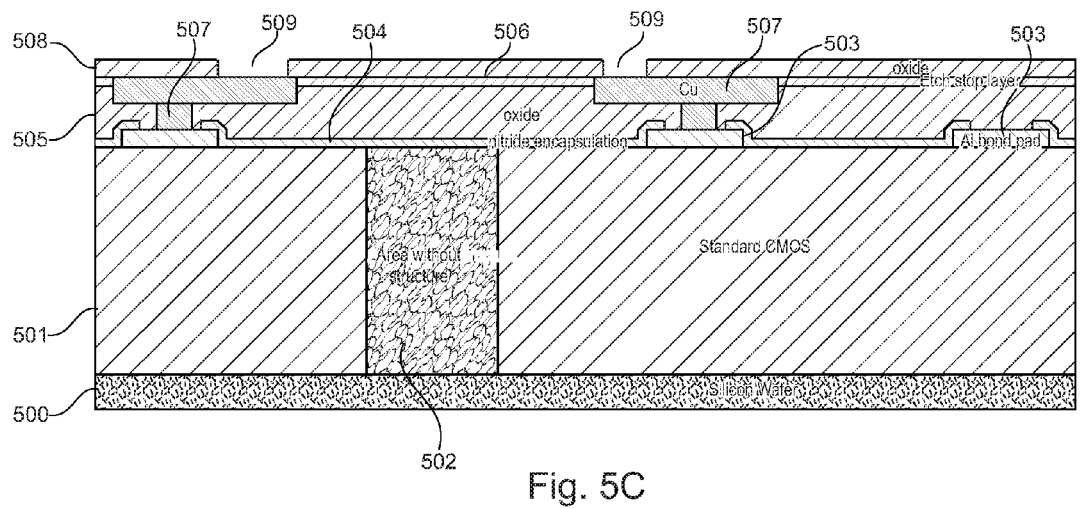

FIG. 5C shows the multilayer structure of FIG. 5B after some further processing steps, in which a further dielectric layer 508, e.g. silicon oxide, is deposited on top of the etch stop layer 506 and is afterwards patterned in order to uncover at least some portions of the metal level 507 again by forming recesses 509. It should be noted that with respect to FIG. 5C to FIG. 5H a method of forming a stack of sensing layers is described which is slightly different in the steps as the method described with respect to FIG. 2A to FIG. 2D.

Figure 5D:
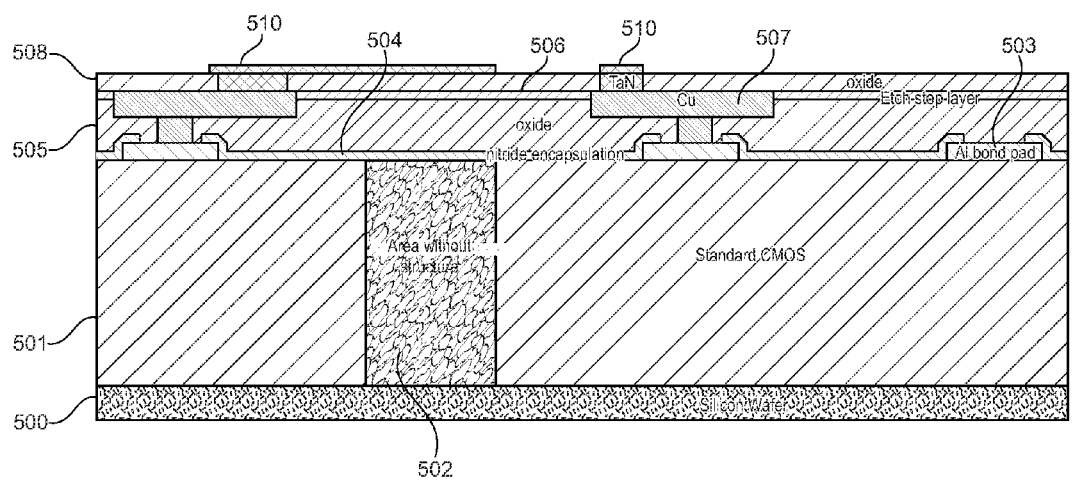

FIG. 5D shows the multilayer structure of FIG. 5C after some further processing steps, in which a layer 510 of conductive material is deposited on top of the dielectric layer 508 and the recesses 509, wherein the conductive material may be TaN, for example. The layer 510 may be a first sensing layer. The conductive layer 510 may then be planarized, e.g. by CMP, and may afterwards be patterned, in order to only leaving areas covered or filled with the conductive material, which are formed into sensing layers or contact areas for sensing layers afterwards. In particular, the conductive layer 510 may remain in regions of the metal layer 507 or in areas above the unstructured areas 502 of the integrated chip 501.

Figure 5E:
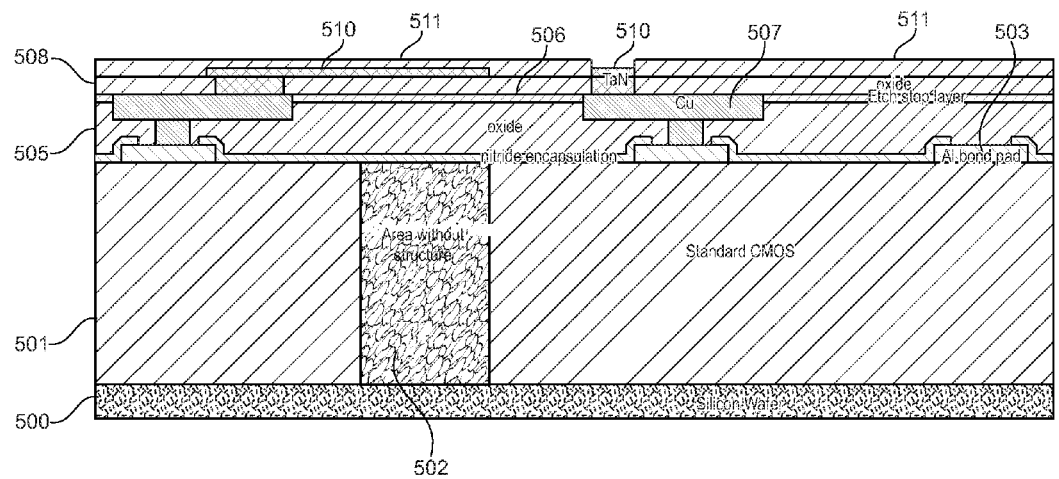

FIG. 5E shows the multilayer structure of FIG. 5D after some further processing steps, in which a further dielectric layer 511 is deposited comprising silicon oxide, for example to cover the conductive layer 510 and to provide an insulating layer with respect to a further sensing layer. The dielectric layer 511 may then be patterned, e.g. etched, in order to uncover portions of the conductive layer 510 again, in order to enable the contacting of the first sensing layer. The uncovered portions may in particular correspond to the areas where the recesses 509 where formed and filled with the conductive layer, i.e. in regions which are arranged above the metal level 507.

Figure 5F:
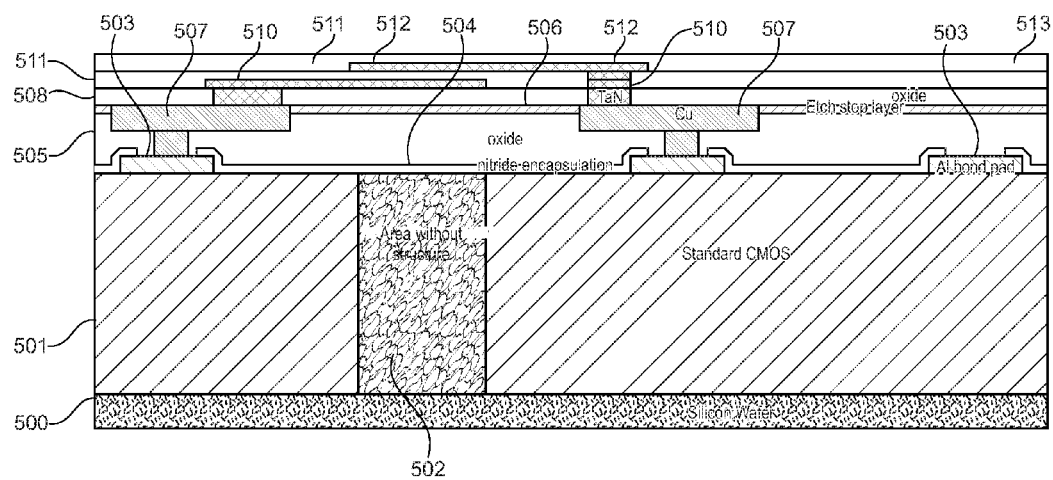

FIG. 5F shows the multilayer structure of FIG. 5E after a further deposition step in which a further metal layer 512 is formed which after some patterning may form a second sensing layer and a contact area of the same. The metal layer 512 is afterwards planarized, e.g. CMP, etched in a similar way as described with respect to FIG. 5D, i.e. to form the second sensing layer above the unstructured area 502 and to provide a contact to the same. After the patterning step a dielectric covering layer 513 is formed.

Further steps as described with respect to FIG. 5D and FIG. 5E may be repeated in order to provide more than two sensing layers. For the sake of clarity of this description and the FIG. 5 the number of sensing layers is restricted to two.

Figure 5G:
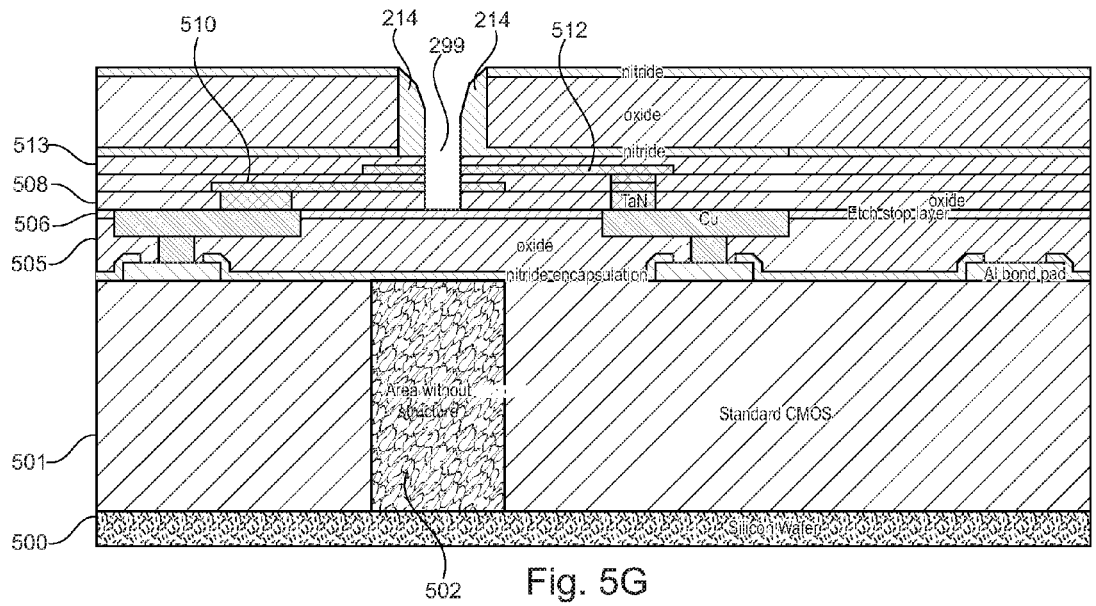

With respect to FIG. 5G the creation of a nanopore 299 is shown. However, as the forming of the nanopore is similar to the process as described in context to FIG. 2 a detailed description is omitted. In general, a dielectric cover layer is formed on the structure shown in FIG. 5F and a primary hole is formed above the unstructured area 502. Afterwards a narrowing layer 214, e.g. comprising silicon nitride, is formed on and in the primary hole. Then the stack of sensing layer is patterned, e.g. etched, by using the spacer formed by the narrowing layer as a mask, wherein the patterning is stopped at the etch stop layer 506. This patterning forms the nanopore in the region of the stack of sensing layers.

Figure 5H:
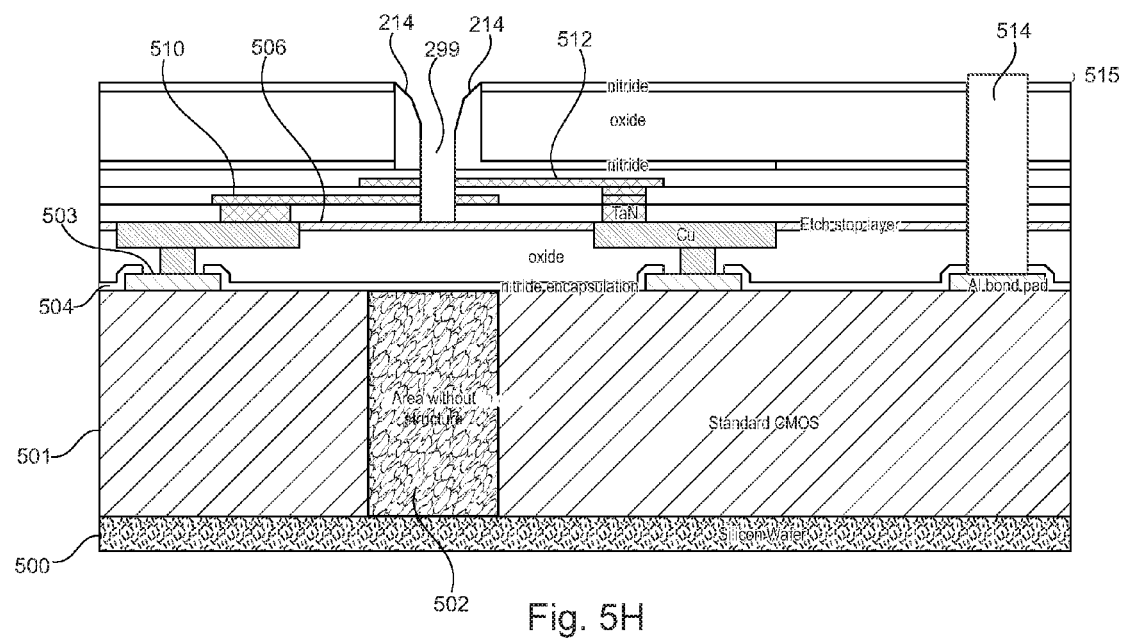

With respect to FIG. 5H a bond pad opening is shown, i.e. a patterning uncovering at least some of the of the bond pads 503 in order to contact them by a conductive layer 514. This opening may be done by an etching step as well. If necessary, the nanopore may be protected during this etching step by a protection layer, e.g. by a sacrificial layer, if an additional metal layer is needed on top, or a lift off technique is used. However, the additional metal layer may also stay like this, i.e. projecting as depicted in FIG. 5H, since the difference in height 515 between the bond pads and the top layer may only be a few micrometer which may not cause any problems. Another solution may be to make the contacts from the backside after a backgrinding.

Figure 5I:
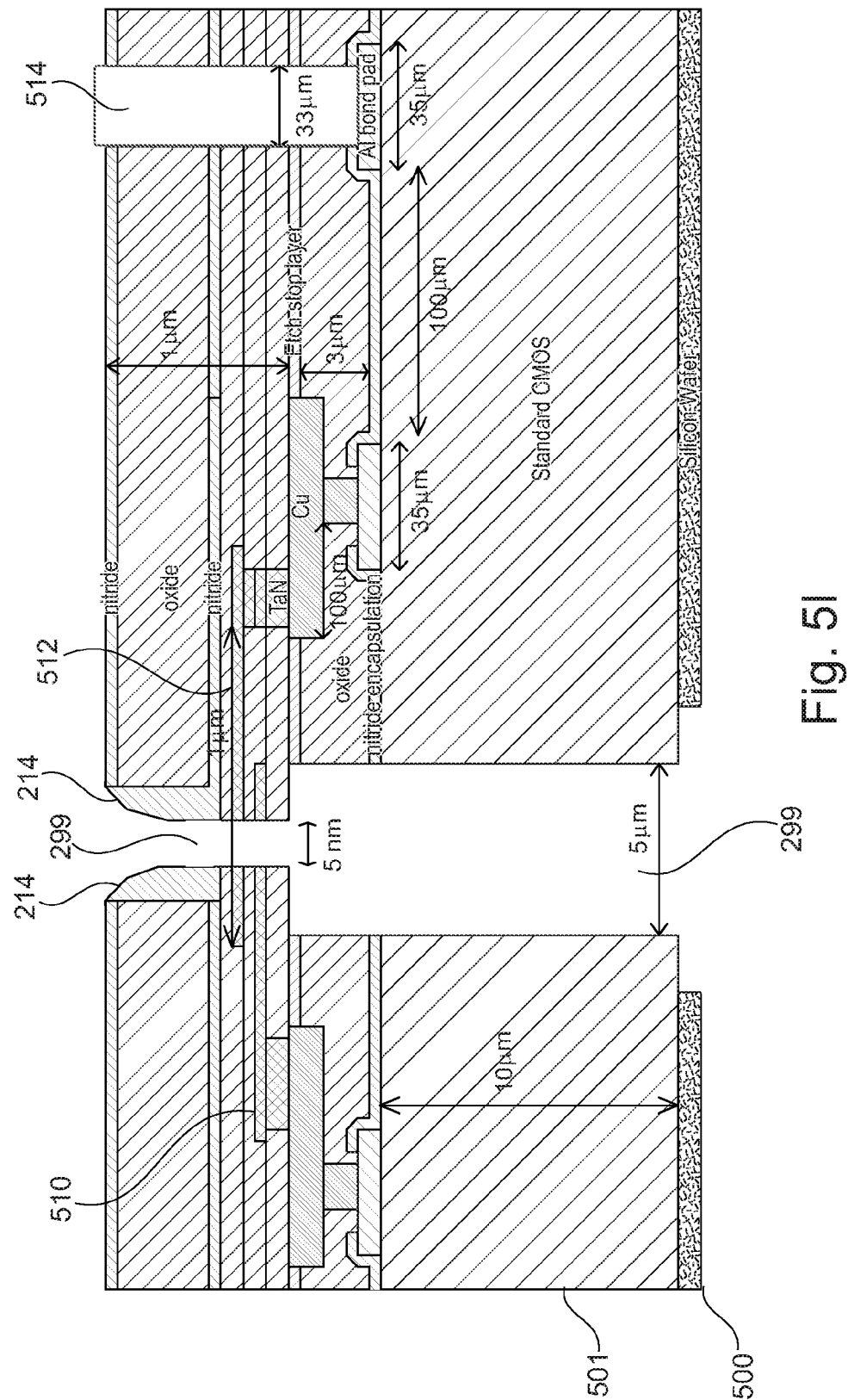

With respect to FIG. 5I further steps of opening the nanopore, i.e. to provide a through hole are described. In a first step a backgrinding of the substrate 500 is performed which is followed by a patterning step of the unstructured area 502. In this patterning step, e.g. etching step, the unstructured area is removed as well as the encapsulation layer 504 and the dielectric layer 505 in this area. The etch stop layer 506 may perform as an etch stop in this etching step. Afterwards the etch stop layer is removed in the area to open the nanopore so that a channel through the structure shown in FIG. 5 for a fluidic sample is provided. Additionally, some exemplary dimensions are given in FIG. 5I as well. In particular, the cross sectional size of the nanopore in the area of the stack of sensing layers is in the order of 5 nm while the channel through the substrate and the integrated circuitry level 501 may be in the range of 5 micrometer. The lateral size of the bond pads may be in the range of 35 micrometer, while the distance between bond pads may be in the range of 100 micrometer. The thickness of the dielectric layer 505 may be in the range of 3 micrometer, while the thickness of the integrated chip 501 may be in the range of 10 micrometer. The thickness of the multilayer structure 550 may be in the range of 1 micrometer, while the lateral extension of each sensing layer may be in the range of 1 micrometer. Additionally, the width of the contact lines contacting the bond pads may be in the range of 33 micrometer. However, it should be stressed that these numbers are just exemplary dimensions which may be altered in a wide range according to the specific needs. In an alternative embodiment, the contact to the bond pads may be done at the backside instead of the front side, for example by through silicon via techniques.

It should be noted that although two sensing layers are described with respect to the figures it is of course possible to use another number in particular a greater number of sensing layers. Furthermore, it should be noted that a sensor array may be manufactured comprising a plurality of stack of stack of sensing layers with corresponding holes or nanopores. Additionally, it is noted as well that of course other materials than the described are possible. Furthermore, it should be noted that the specific materials stated in the above description are just exemplary, e.g. instead of TaN as the conductive material of the sensing layers every other suitable conductive material can be used.

The above described sensor device comprising a stack of sensing layers may be suitable to perform a detection or sampling based on voltage changes in the sensing layers, tunneling current between two sensing layers or resonant tunneling, or impedance measurement between two sensing layers. Since a small distance between two following sensing layers is possible it may be possible to even identify or distinguish monomers of a polymer which are very close together, like bases in a DNA strand. Furthermore, the redundant measurement with the different sensing layer may reduce an ambiguity which may arise out of the motion of the fluidic sample, since the moving velocity and/or the moving direction of the fluidic sample may vary, which might, in case no redundancy due to several sensing layers is provided, lead to the fact that it is not clear whether the fluidic sample comprises several times the same monomer or whether the same monomer is measured several times. Additionally, it may be possible to improve a parallel processing, since it may be possible to provide arrays of stacked sensing arrangements which do not need separate off-chip electronic, like processing and amplification. In particular, some described embodiments may have the following advantages:

the distance between sensing layers can be very small and very precise possibly leading to a better distinction between the DNA bases, a large number of sensing layers may be included, possibility to etch a hole of a few nm in a relatively "high" layer, where several sensing layers or a detection system can be included possibly leading to a sequential reading, possibility to make an array instead of a discrete device because a circuitry with several metal levels is possible possibly leading to an improved parallelism, possibility of latter statistical and error-cancellation treatment because the DNA will face several sensing layers one after each other in each nanopore and several nanopores in parallel may screen several DNA strands, possibility to integrate CMOS so that on-chip amplification (for example by an integrated Sauty bridge) and on-chip signal processing may be possible, and conventional litho techniques may be used instead of e-beam, ion-beam or ion-beam with sculpting.

Furthermore, it should be noted that preferably connection paths or connection links to the sensing layers may be short and/or the respective connection points between a bond pad and the sensing layer may be arranged close to the nanopore so that it may be possible to reduce parasitic capacitance or high resistance of the stacked sensing arrangement. Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A sensor device for analyzing components of a fluidic sample, the sensor device comprising:
    a multilayer structure comprising:
    a nanopore formed therein which is adapted to let pass the fluidic sample, the nanopore having a cross-section dimension of less than 20 nanometers;
    a stacked sensing arrangement arranged in such a way that the fluidic sample passes the stacked sensing arrangement when the fluidic sample passes the nanopore, the stacked sensing arrangement comprising at least three sensing layers which are arranged above each other and which are electrically insulated from each other by a dielectric layer arranged between two sensing layers, wherein the sensing layers have a thickness of less than 10 nm and wherein the dielectric layer has a thickness of less than 10 nm between two sensing layers;
    a cover layer over the stacked sensing arrangement, the cover layer having a sidewall that forms a primary hole over the nanopore, said primary hole having a cross-section dimension that is larger than the cross-section of the nanopore; and
    a sidewall spacer formed on the sidewall of the cover layer, the sidewall spacer having a dimension that reduces the cross-section dimension of the primary hole.

2. The sensor device according to claim 1, further comprising:
    an integrated circuit arrangement formed on a substrate and coupled to the sensing layers of the stacked sensing arrangement, wherein the sensing layers are formed on top of the integrated circuit arrangement.

3. The sensor device according to claim 1, wherein at least one of the sensing layers is adapted to actuate the fluidic sample.

4. A sensor array for analyzing components of a fluidic sample, the sensor array comprising:
    a plurality of sensor devices according to claim 1.

5. The sensor device according to claim 1, wherein the dimension of the sidewall spacer is such that the reduced size of the primary hole has a dimension that matches the cross-section dimension of the nanopore.

6. The sensor device according to claim 5, wherein the nanopore has a cross-section dimension of less than 2 nanometers.

7. A method of manufacturing a stacked sensing arrangement for a sensor device for analyzing components of a fluidic sample, the method comprising:
    providing a multilayer structure comprising a stacked sensing arrangement, and a cover layer covering the stacked sensing arrangement, said stacked sensing arrangement comprising at least three sensing layers which are arranged above each other and which are electrically insulated from each other by a dielectric layer arranged between two sensing layers, wherein the sensing layers have a thickness of less than 10 nm and wherein the dielectric layer has a thickness of less than 10 nm between two sensing layers;

forming a primary hole through the cover layer, wherein the primary hole is formed by a sidewall of the cover layer, the primary hole having a cross-section dimension;

narrowing the cross-section dimension of the primary hole by forming a spacer layer on the sidewall of the cover layer; and forming a nanopore through the stacked sensing arrangement at the location of the primary hole, wherein the nanopore has a cross-section dimension of less than 20 nm and is adapted to let pass the fluidic sample.

8. The method according to claim 7, wherein the multilayer structure is provided on a substrate.

9. The method according to claim 7 further comprising:
forming contact terminals adapted to contact the stacked sensing arrangement.

10. The method according to claim 7, further comprising:
integrating CMOS electronic elements in the multilayer structure.

11. The method according to claim 7 wherein forming the nanopore comprises etching through the multilayer structure and using the spacer layer as an etching mask during the etching.

12. The method according to claim 11, wherein the spacer layer is formed by chemical vapor deposition.

13. The method according to claim 12, wherein the nanopore is formed such that its cross-section dimension matches the dimension of the narrowed primary hole.

14. The method according to claim 13, wherein the nanopore has a cross-section dimension of less than 2 nanometers.

* * * * *